(12) United States Patent
Groves et al.

(10) Patent No.: US 7,190,895 B1
(45) Date of Patent: Mar. 13, 2007

(54) PHOTOGRAPHIC IMAGING SYSTEM FOR BRACHYTHERAPY DEVICE VERIFICATION

(75) Inventors: Matthew T. Groves, Alpharetta, GA (US); Jack C. White, Alpharetta, GA (US); James C. Cauthen, Lilburn, GA (US)

(73) Assignee: Theragenics Corporation, Buford, GA (US)

( * ) Notice: Subject to any disclaimer, the term of this patent is extended or adjusted under 35 U.S.C. 154(b) by 697 days.

(21) Appl. No.: 10/718,950

(22) Filed: Nov. 21, 2003

(51) Int. Cl.
*G03B 17/56* (2006.01)
*G06K 9/00* (2006.01)

(52) U.S. Cl. .................. 396/429; 396/661; 382/143
(58) Field of Classification Search ................ 396/429, 396/661; 382/141, 143; 378/57, 62, 63, 378/210
See application file for complete search history.

(56) References Cited

U.S. PATENT DOCUMENTS

| | | | |
|---|---|---|---|
| 4,758,888 A | 7/1988 | Lapidot | 348/91 |
| 5,617,171 A * | 4/1997 | Ishikawa et al. | 396/512 |
| 6,530,875 B1 | 3/2003 | Taylor | 600/7 |
| 6,574,580 B2 | 6/2003 | Hamilton | 702/128 |
| 7,072,440 B2 * | 7/2006 | Mario et al. | 378/57 |
| 2002/0046010 A1 | 4/2002 | Wessol | 703/2 |
| 2002/0091315 A1 | 7/2002 | Spetz | 600/407 |
| 2004/0149823 A1 * | 8/2004 | Aptekar | 235/385 |

* cited by examiner

*Primary Examiner*—W. B. Perkey
(74) *Attorney, Agent, or Firm*—Knoble Yoshida & Dunleavy, LLC

(57) ABSTRACT

A photographic imaging system and method for brachytherapy device verification is disclosed. The method involves receiving an order from a customer; loading a container with materials according to the order to create a loaded container; making a photographic image of the loaded container; and using the photographic image to verify that the order and the loaded container match. The verification system employs an order form, a photographic imaging device and apparatus for associating information with the photographic image to provide verification that an order has been filled correctly. Also disclosed is a brachytherapy system including at least one container containing radioactive brachytherapy materials, an order form and at least one photographic image of said at least one container showing the radioactive brachytherapy materials. The brachytherapy system of the invention ensures easy, safe and essentially error-free verification that orders for brachytherapy materials have been properly filled.

19 Claims, 6 Drawing Sheets

Needle Configuration Form        Ship Date:

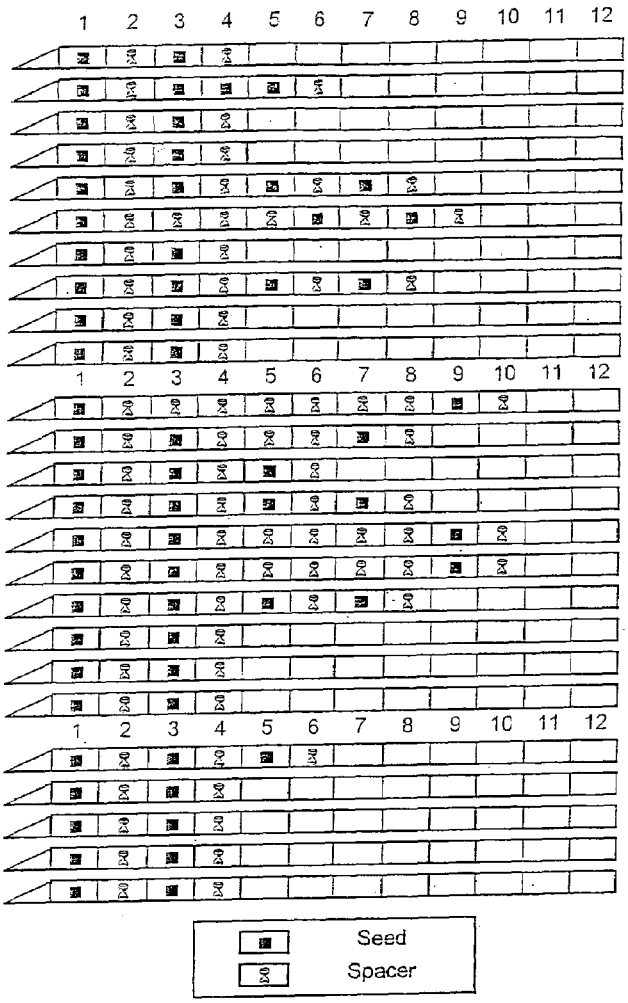

| Needle Number | Product Code | Number of Spacers | Number of Seeds |
|---|---|---|---|
| Tray 1 | | | |
| 1 | TS222 | 2 | 2 |
| 2 | TS224S | 2 | 4 |
| 3 | TS222 | 2 | 2 |
| 4 | TS222 | 2 | 2 |
| 5 | TS224 | 4 | 4 |
| 6 | TS223S | 6 | 3 |
| 7 | TS222 | 2 | 2 |
| 8 | TS224 | 4 | 4 |
| 9 | TS222 | 2 | 2 |
| 10 | TS222 | 2 | 2 |
| Tray 2 | | | |
| 11 | TS222S | 8 | 2 |
| 12 | TS223S | 5 | 3 |
| 13 | TS223 | 3 | 3 |
| 14 | TS224 | 4 | 4 |
| 15 | TS223S | 7 | 3 |
| 16 | TS223S | 7 | 3 |
| 17 | TS224 | 4 | 4 |
| 18 | TS222 | 2 | 2 |
| 19 | TS222 | 2 | 2 |
| 20 | TS222 | 2 | 2 |
| Tray 3 | | | |
| 21 | TS223 | 3 | 3 |
| 22 | TS222 | 2 | 2 |
| 23 | TS222 | 2 | 2 |
| 24 | TS222 | 2 | 2 |
| 25 | TS222 | 2 | 2 |
| Totals | | 83 | 66 |

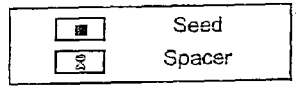
■ Seed
⊠ Spacer

| Product Code | Number of Seeds |
|---|---|
| | |
| TS200 | |
| TS202 | |
| | |
| | |
| | |
| Totals | 0 |
| Grand Totals | 83 · 66 |

Facility:

Radiation Oncologist:

Implant Date:

Patient Name:

Translator:

Verifier:

Scheduling: _____

TGX Order #: _____

This package insert is designed to provide a description of the seed and spacer configuration as ordered by the customer. The health care professional must verify seed/spacer configuration prior to the procedure.

Fig. 5

PHOTOGRAPHIC IMAGING SYSTEM FOR BRACHYTHERAPY DEVICE VERIFICATION

BACKGROUND OF THE INVENTION

1. Field of the Invention

The invention relates to a method of using photographic imaging technology to verify the arrangement of materials provided to fill orders for brachytherapy treatments.

2. Description of the Related Technology

Brachytherapy is used in the treatment of numerous types of cancers, including cervical, breast, lung, head, neck, and prostate. Brachytherapy has also been employed in treating eye maladies. Brachytherapy treatments require the usage of radioactive materials. These radioactive materials are used in various devices that are employed in the field of brachytherapy for medical procedures. An example of such a device is a needle for inserting brachytherapy seeds and biocompatible spacers into a patient. These needles require a specific arrangement of the seeds and spacers depending on the treatment profile and desired radiation dosage for a patient. A medical professional has to place an order for the desired treatment profile. Such custom orders require a variety of configurations of the brachytherapy materials. Due to the harm that an incorrect radiation treatment can cause, it is important to verify that an order has been correctly filled before using a device on a patient. Additionally, the law requires third-party verification that an order has been filled correctly by a party other than the company filling the order before using any ordered material. Current methods to ensure quality control are subject to high error rates.

The verification process can be accomplished manually. However, there are many drawbacks to verifying the orders manually. Due to the radioactive nature of the materials, extended exposure to the materials is highly undesirable. This results in personnel working at a rapid pace during such manual verification in order to diminish the potential radiation exposure. This, in turn, increases the number of errors that occur when manually verifying orders.

Radiography is the industry standard method for verifying orders. The containers containing the radioactive materials are imaged using X-rays. A copy of the X-ray image can then be attached to the packaged order and it can be used to verify the order. This method is effective for providing information regarding the location of certain materials in an order, however the quality of the image produced is not high, spacers, needles and other components typically cannot be identified in such images since they do not create a viewable X-ray image, and mistakes can occur from not interpreting the image properly. The poor quality of the image and the difficulties encountered in attempting to interpret the image, results in a relatively large number of errors during the verification process.

Another verification method is disclosed in U.S. Pat. No. 6,530,875 B1 to Taylor et al. In col. 12, line 65–col. 13, line 14 and FIGS. 7A–7c, a needle loading report is disclosed that provides the spatial orientation of the seeds and spacers in each needle, as well as the number of radioactive seeds per needle. This report permits a customer to audit a shipment. In particular, a transparent wall of the tubular sleeve permits a person to compare the contents of each needle with the needle report. This allows a report to be created with a reduced amount of radiation exposure to the person creating the report. Although the report is highly detailed, it still requires a person at the loading end to fill it out correctly which can lead to human error.

Therefore, there remains a need for a method of verification that provides an easy way to verify the contents of an order, which minimizes human exposure to potentially harmful radiation and that further reduces the chance of human error.

SUMMARY OF THE INVENTION

Accordingly, it is an object of certain embodiments of the invention to provide an easy way to verify the contents of an order, while minimizing exposure to potentially harmful radiation, and that reduces the chance of human error.

In order to achieve the above objects of the invention, a photographic imaging system and method for verification is used. In a first aspect, the invention relates to a method for verifying orders for brachytherapy devices. The method involves receiving an order from a customer, loading one or more containers with materials according to the order to create a loaded container; making a photographic image of the one or more loaded containers; and using the photographic image to verify that the order and the one or more loaded containers match.

In another aspect, the invention relates to a system for filling and verifying orders for brachytherapy devices that includes materials for use in brachytherapy devices; one or more containers for loading the materials according to an order to create one or more loaded containers; a photographic imaging device for taking a photographic image of the one or more loaded containers; and a copy of the photographic image to verify that the order and the one or more loaded containers match.

In another aspect, the present invention relates to a brachytherapy system including one or more containers containing brachytherapy materials, an order form, and a photographic image for verification of the order.

These and various other advantages and features of novelty that characterize the invention are pointed out with particularity in the claims annexed hereto. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 5 is an example of a custom configuration form.

DETAILED DESCRIPTION OF THE PREFERRED EMBODIMENT(S)

The invention provides a method and system for the verification of orders placed for brachytherapy devices in order to reduce the error rate in filling and verification of orders during the production process, as well as the verification process conducted by the end user. Use of the method described below is expected to significantly reduce the number of errors in the filling and verification of orders for brachytherapy devices, when compared to prior art methods.

Figure 1:
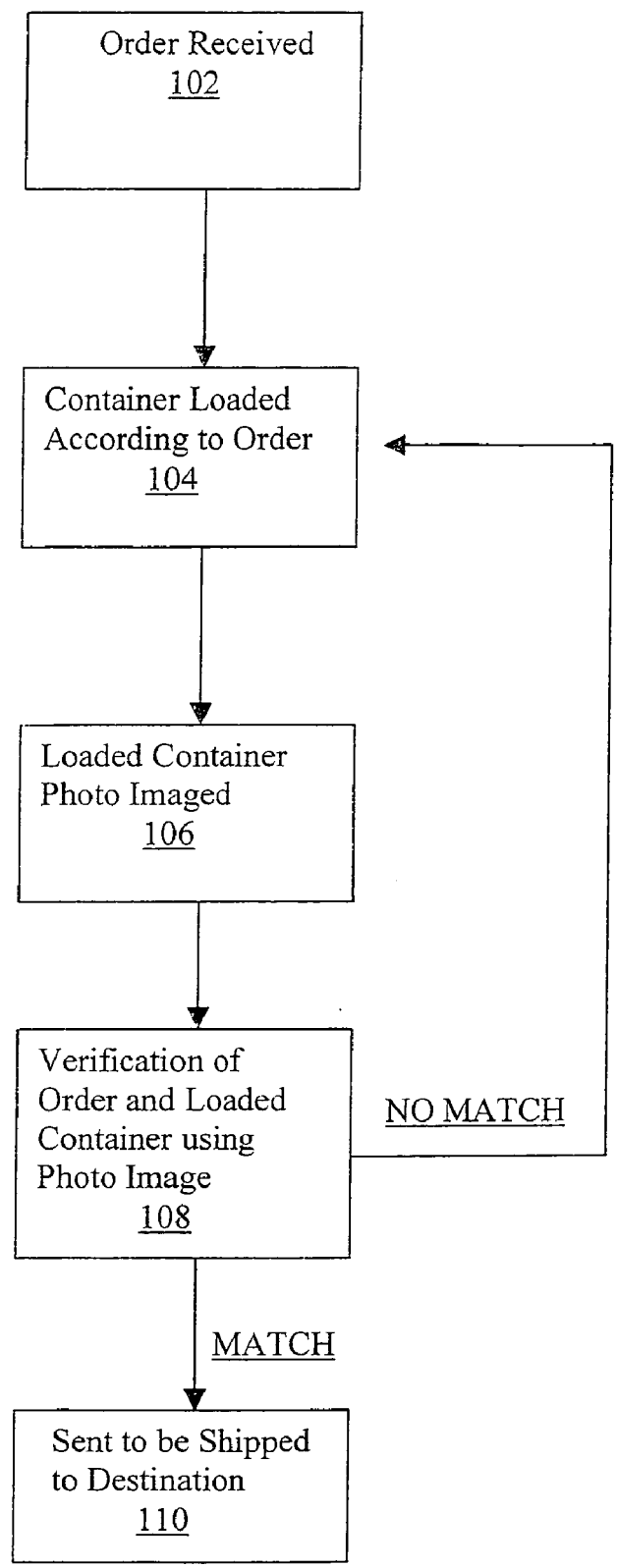
FIG. 1 is a flow chart of the verification method.

FIG. 1 is a flow chart showing one embodiment of a verification of the invention. In step 102 an order is received from a customer for a brachytherapy device. The order will typically be for a certain amount of material, some of which will be radioactive. In the preferred embodiment, used for this example, the order is to be filled with biocompatible spacers and radioactive brachytherapy seeds to be used with a brachytherapy needle. However, the method and system can be used with a variety of other brachytherapy devices besides brachytherapy needles and needle cartridges. The system and method can also be used with brachytherapy needles, Mick® magazines or similar brachytherapy magazines, radioactive sources for the treatment of macular degeneration, IVBT (intervascular brachytherapy treatment) sources, or seed strands, for example.

In step 104, one or more containers are loaded with the materials in compliance with the order. In preferred embodiments the container is a needle, needle cartridge, magazine or seed strand that is to be loaded with a customized combination spacers and radioactive seeds. These spacers and seeds are loaded in the customized configuration required by the order.

In step 106, the one or more loaded containers are photographically imaged. In the preferred embodiment, this is accomplished with a digital imaging device arranged to record a digital image of the loaded container. A digital image is preferred due to the ease with which it can be stored, processed and transmitted via computers. However, it is within the scope of the present invention to employ other types of photographic images, as long as they provide a visual representation of the contents of the one or more containers using visible light.

A significant advantage of photographic imaging is that it avoids the need to use an X-ray imaging device thereby decreasing costs, eliminating the need to have a special X-ray imaging device at the manufacturer's location for this purpose, and reducing the potential for exposure of personnel to X-ray radiation during the X-ray imaging process. Another advantage of photographic imaging is that the imaging steps can be fully automated to thereby eliminate human intervention in the imaging steps. The advantage of this is that this will reduce the potential for exposure to harmful radiation from the radioactive material that would otherwise occur if manual inspection were performed.

In step 108, the photographic image is used to verify the contents of the one or more containers. A copy of the order and the photographic image are compared in order to determine if there are any discrepancies. If the photographic image and the order match then the order can be sent to shipping so that it can be shipped to its destination. A significant advantage of this step in the process is that the person verifying the order at the manufacturer need not directly handle the order to verify it since verification is accomplished by comparison of the order form with a photographic image of the order. Again, this significantly reduces the amount of radiation exposure at the manufacturer's site relative to manual inspection of the order.

In step 110, the order is shipped to a destination specified in the order. Upon arriving at the destination, typically a hospital, a copy of the photographic image can be compared to the order form to verify that the contents of the order are correct. Also, if the photographic image is damaged or missing, an electronic version of the missing image can be instantaneously transmitted to the customer's location for immediate verification of the order. This step also has the significant advantage that this legally mandated third party inspection of the order can be carried out without directly handling the radioactive material, which provides the ability to fully comply with the law without the potentially harmful exposure of personnel to radiation from the order.

Figure 2:
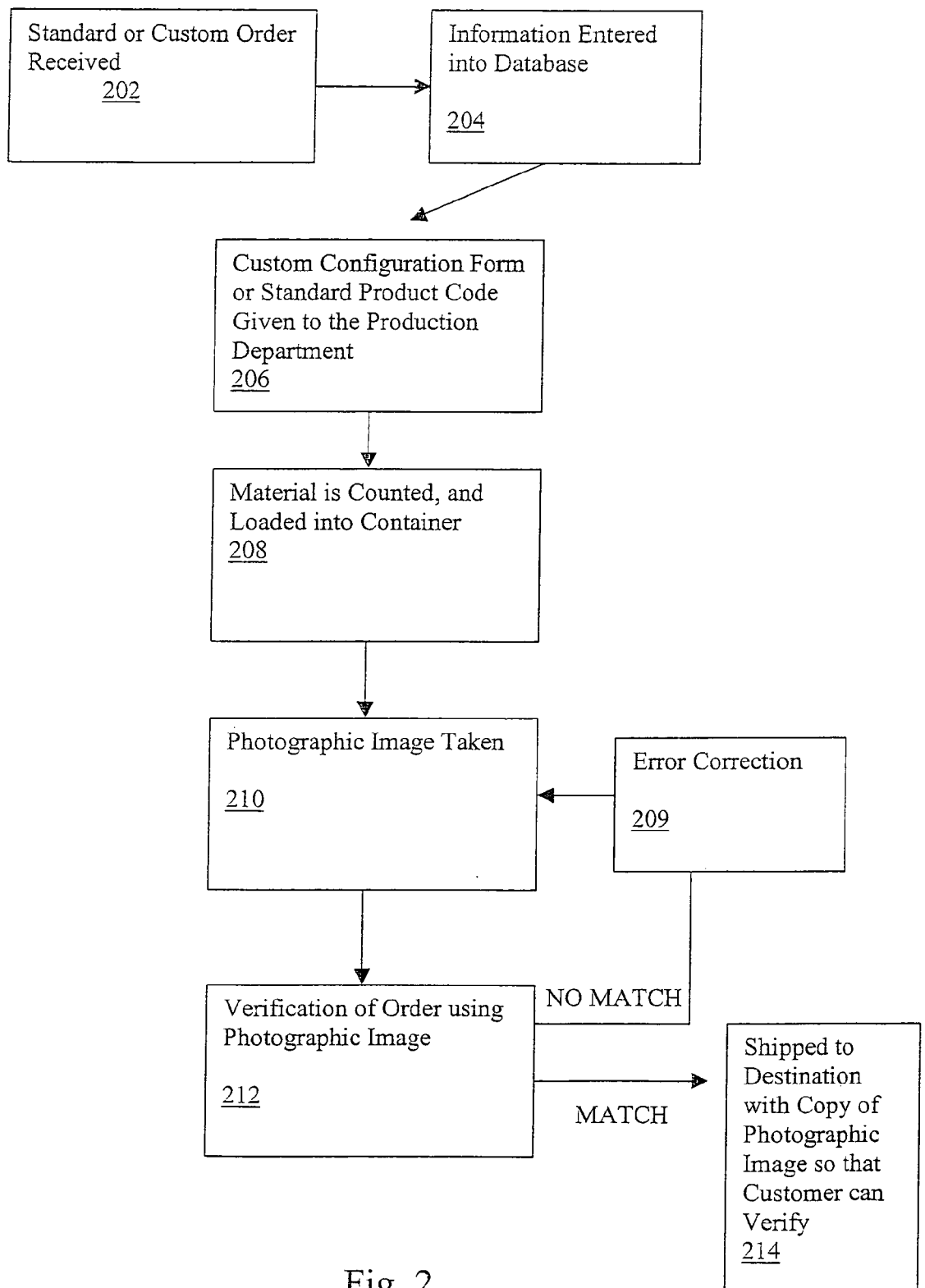
FIG. 2 is a detailed flow chart of the steps performed after receipt of the order.

FIG. 2 is a flow chart that provides additional detail about the various types of ordering processes, which may be encountered in commercial practice when performing step 102 of the method of FIG. 1. Step 202 is receipt of the order. The order can either be a standard order or a custom order to fill one or more containers. All standard orders are filled with seeds and spacers in an alternating arrangement. The first position in a container will generally contain a seed, then a spacer, then another seed, etc. There are several possible configurations in a standard order, represented by different product codes. To place a standard order a customer may simply request a given quantity of each product code. In a custom order the customer must fill out a detailed custom configuration form, as shown in FIG. 5. This form shows the seed/spacer configuration required for each needle or container to be used in the treatment process. In a custom order the customer can request any combination of seeds and spacers for each container.

The order in step 202 may be received by phone, or fax. Additionally the order could be received via the Internet by filling out an on-line order form. When an order is placed on-line, the order information can be routed directly into the order database and an order number can be automatically assigned. The on-line system can also provide e-mail notification of order receipt, and, if desired, an additional e-mail notification upon shipping of the order. The e-mail notification given upon shipping of the order can include a copy of the photographic image. This provides an opportunity for immediate inspection by the customer to ensure that the order was filled correctly. An option can be provided by the on-line system to additionally allow a certain amount of time for response prior to shipping in order to allow for customer feedback should the customer determine from the photographic image that the order has not been filled correctly or that the order itself is incorrect. Alternatively, the customer can request that no orders are shipped until a positive verification of the photographic image is sent back to the shipping department or until a given time period for response has lapsed. Of course, even if an on-line system is not employed, the photographic image can still be sent to the customer prior to shipping for verification of the order by the customer, if desired.

In step 204 the order information is entered into a database. This is done manually when an order is received via telephone, e-mail or on paper. Alternatively, when the order is received via the Internet, the order information can be routed directly to the database in step 204. Upon entry of the information into the database, the appropriate amounts of the required materials are allocated for loading into the one or more containers and, optionally, the current inventory record is updated to reflect the use of these materials. In the preferred embodiment, the appropriate number of seeds and spacers will be allocated for loading into the one or more containers.

In step 206, the custom configuration form or standard production code is given to the production department. For a standard order, the order form includes the quantity of each standard product code. For a custom order, the custom configuration form includes the quantity and positioning information for the materials. Alternatively the order or custom configuration form can be accessed from a database such as a computer network.

In step 208, the appropriate amount of material is counted, and loaded into the one or more containers to fill the order. This can be done either by hand or by an automated loading mechanism. After loading the several containers required to fill a typical order, a plurality of containers are arranged in a package such as a tray. A tray is preferred since it serves to hold the containers in a predetermined order and the containers are held in a manner whereby all containers can be photographed, in order, in a single photograph. Other holding devices besides trays can be used although such devices should both hold the containers in a specific order relative to one another and hold the containers in such a manner that a single photograph can capture an image of the contents of all of the containers in a single holding device. Preferably, the tray includes a radiation shielding device or can be inserted into a radiation shielding device.

A typical shipping container will include radiation shielding forming at least part of the housing of the shipping container in order to contain radiation emitted by the brachytherapy devices and thus typically radiation shielding is provided by the shipping container into which one or more packages or trays can be inserted for shipping.

In the preferred embodiment step 208 is accomplished by first counting out the appropriate number of seeds and spacers. Then the seeds and spacers are loaded into several containers as indicated by the order form, and the containers are placed in a tray or other suitable device for holding the containers.

In step 210, a photographic image is taken. In the preferred embodiment the photographic image is a digital photograph taken with a camera connected to a computer. This permits the photographic image to be automatically stored in a permanent file associated with the order to assist the producer in maintaining a detailed record of all orders that have been shipped. Alternatively, a photographic image can be taken and scanned into a computer system. A copy of the photographic image can then be included in the shipment of the order.

In one embodiment, a plurality of loaded containers are placed in a package or tray in the order specified by the order form. The package or tray preferably has a retractable radiation shielding device which is closed for handling the package or tray but which is opened for taking the photographic image. The preferred package or tray has a radiation shielding device which can be opened and closed by an automated system such that the step of taking the photographic image can be carried out with little or no human intervention to thereby minimize potential exposure to radiation.

In step 212, the photographic image is used for the verification of the order. A copy of the photographic image is compared with the order to determine if there is a match. If there is not a match then the filled order will be sent to step 209 to correct the error. If there is a match then the order can be sent to shipping step 214.

In step 214, the order is sent to the customer with a copy of the photographic image. The customer can then take the photographic image and use it to verify that it corresponds with the order placed in order to verify that the order has been filled correctly. The use of the photographic image allows for verification without having to open the package or shipping container and check manually. This is highly beneficial due to radioactive nature of the materials and the need to keep the materials stored securely. The photographic image is also superior to an X-ray image, because an X-ray image is not as readable as the photographic image and because only certain elements of the contents of the containers will show up on an X-ray image. Typically, for example, spacers do not show up on an X-ray image.

The use of a photographic image is also superior to the use of a detailed manual report, since the preparation of a detailed manual report increases the chance for error relative to taking a photographic image. Alternatively, instead of using a copy of a photographic image attached to the container, the customer could access the photographic image on-line in order to verify that the order has been filled correctly.

Figure 3:
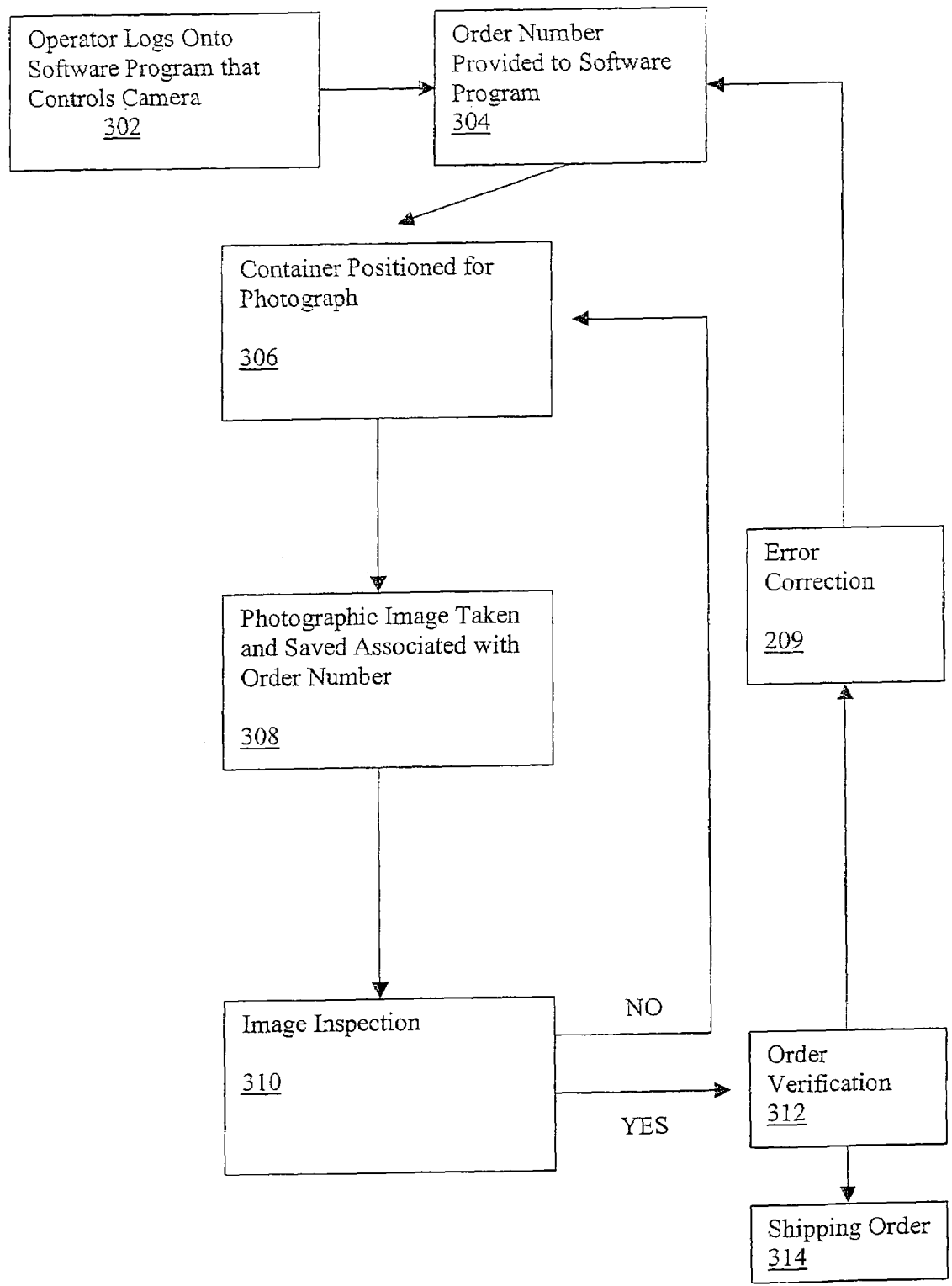
FIG. 3 is a detailed flow chart of the photographic imaging process.

FIG. 3 is a flow chart of a preferred photographic imaging process. In step 302 the operator logs onto a software program that controls the camera. In step 304 the order number is provided to the software program. The order number can be manually entered by the operator or can be scanned from the shipping container label using, for example, a bar code or other similar means. In addition, an optical character reader could be employed to read the order number from the shipping container label shown in FIG. 4. In an especially preferred embodiment, the operator enters the order number and the software program scans the order number and checks it against the order number entered by the operator to ensure that the correct order number is associated with a particular photograph.

In step 306 the package or tray is positioned in front of the camera lens to take the photograph. A shielding panel of the package or tray is then opened to permit an unobstructed view of the materials contained within the package or tray. The shielding is preferably constructed of a material that prevents the emission of harmful radiation, such as lead.

In step 306, it is preferable to ensure that a shipping label is located in the area to be photographed so that at least the order number is visible. Other information can also be provided on the label such as the customer's name and address, the producer's name and address, the trademark or trade name for the product, a description of the product, a bar code or other identifying indicia, etc. This will provide a visual indication in the photographic image indicating which order the photographic image pertains to.

One other item of information that is preferably included in the photographic image in addition to the order number is a designation of the package or tray number for that particular order. In a typical order, 2–4 packages or trays may be required to hold the order. As a result, it is important for verification purposes that the photographic image can be associated with the specific package or tray that has been photographed.

It is also desirable to have the software program include specific items of information on the photographic image, as well as in the database where the image is stored. Useful information that can be provided by the software program are the order number, the package or tray number, the time and date of the photograph, as well as the name of the operator of the equipment.

Figure 4:
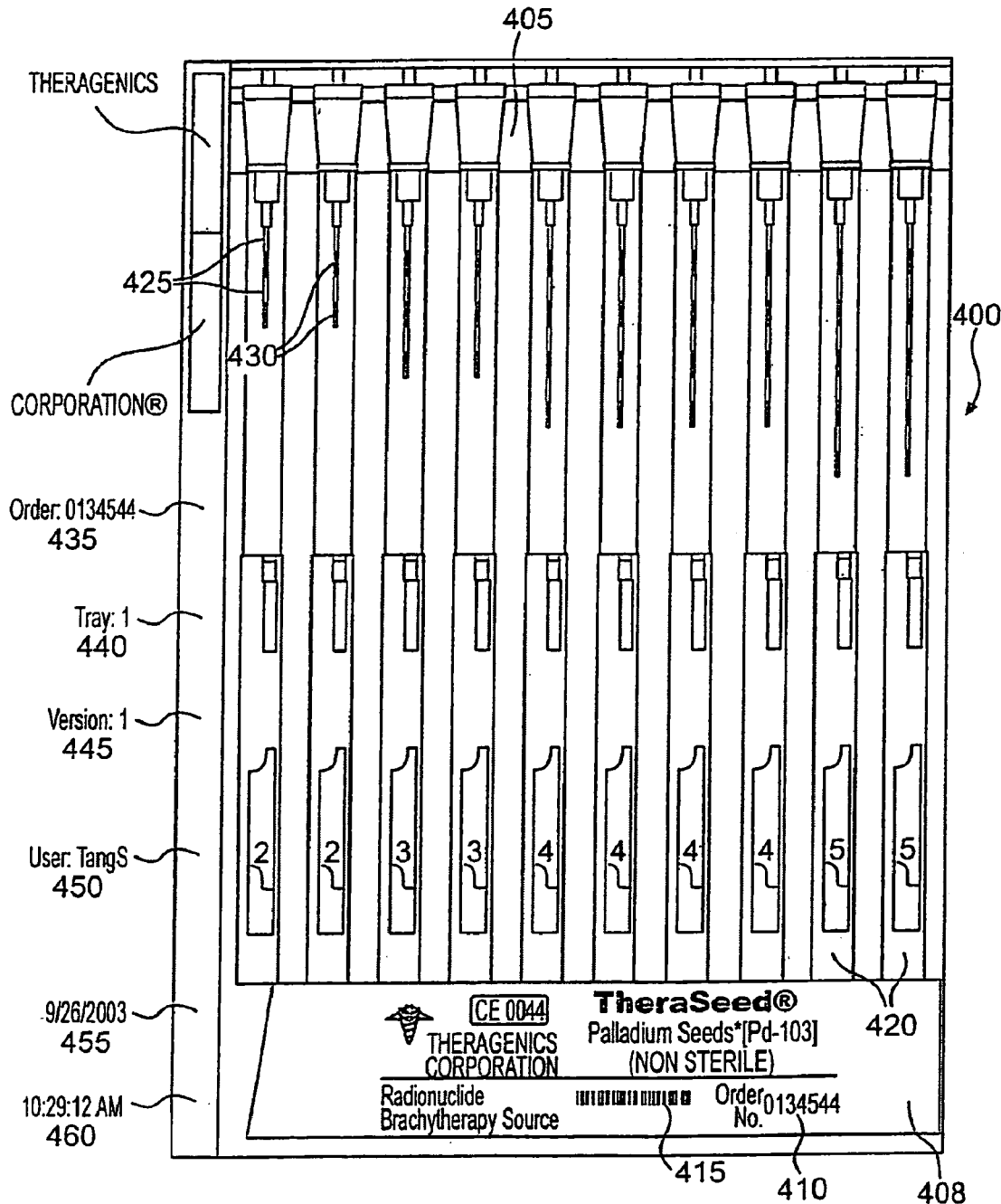
FIG. 4 is an example of a photographic image used for the verification process.

In a more preferred embodiment, information is placed in the photograph both by the software program and by including a copy of the shipping label in the photograph, as shown, for example, in FIG. 4.

In step 308, a photographic image is taken of the contents of the package or tray and then saved with the file associated with the order number for that order.

In step 310, the photographic image is inspected to determine if the image is clear and that the image shows all of the information required for order verification. If the image is of poor quality or does not show all of the requisite information, then the method reverts to step 306 to take another photographic image. This process is repeated until an acceptable image is obtained. In step 312, the photographic image is employed to verify that the order has been properly filled prior to shipping the order to the customer. If the number and arrangement of materials in the photographic image does not match the number and arrangement of materials required by the order, the package or tray will then be returned to the department that loads the containers for correction. The container or containers for which errors have been discovered will then be reloaded and again sent to be photographic imaged. If no errors are found the orders are packaged into shipping containers such as lead pigs for shipment.

It is also possible to electronically send a copy of the photographic image directly to the customer after the order has been verified, thereby providing the customer with notice that the order has been filled, and also providing the customer with an advanced opportunity to verify that the order has been properly filled or that the order itself is correct, prior to shipment of the order, as discussed above. A hard copy of the photographic image can also be produced and stored in a paper file.

FIG. 4 shows an example of a photographic image 400 of a tray 405 with the shielding panel pulled back. Typically the photographic image 400 is in color in order to better distinguish the details of the image 400. In the image the order number 410 can be seen on the shipping label 408. Additionally a bar code 415 may be provided that can be scanned so that each package or tray has its own reference number. Alternatively, a bar code may be provided on the package or tray so that the order number itself does not have to be manually entered into the system, and merely has to be scanned by a bar code reader. The image 400 further shows the various arrangement and numbers of materials to be shipped. Thus, in the image 400 shown in FIG. 4, ten needle cartridges 420 can be seen. Each needle cartridge 420 includes a plurality of seeds 425 (shown in white) and spacers 430 (shown in black). The software has, in this embodiment included in the image 400, the order number at 435, the tray number at 440, the version of the photograph at 445, the operator's name at 450, the date of the photograph at 455 and the time of the photograph at 460.

FIG. 5 shows a form for use with the method. The form shown is an example of the custom configuration order form. With this form a customer can enter the precise arrangement and number of seeds and spacers that he or she desires. On the right hand side of the form a customer can input the desired number of seeds and spacers that should be loaded into the container. This form is then used to load the container with materials in the desired configuration and the amounts necessary for the treatment of a specific patient.

Figure 6:
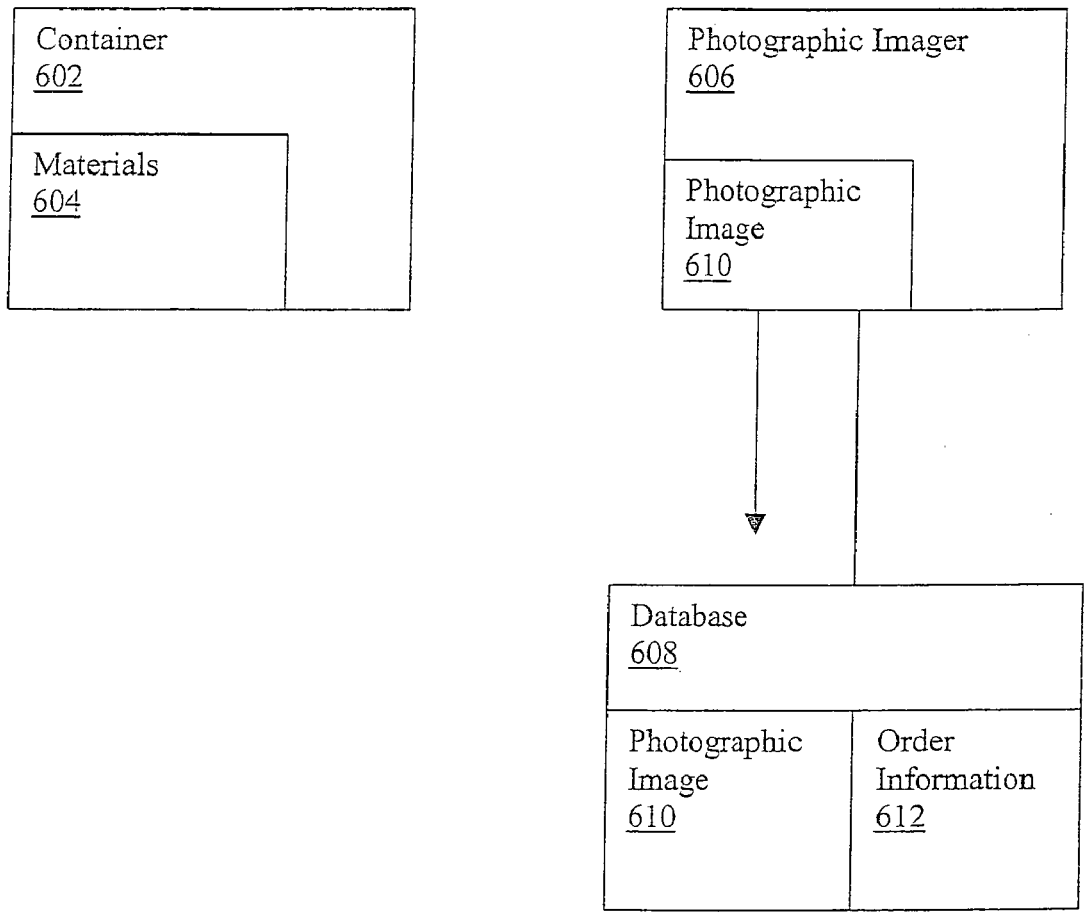
FIG. 6 shows a system that can be used for the verification process.

FIG. 6 shows the components of the verification system of the present invention and the components of the order. A container 602, such as a needle cartridge, a magazine, a seed strand, etc., holds materials 604 which may include, for example, seeds and spacers.

Also shown is the photographic imager 606, which in the preferred embodiment is a digital camera. The photographic imager 606 takes a photographic image 610 of the container 602 with the materials 604 inside. An operator examines the photographic image 610. The operator ensures that the arrangement and number of materials in the photographic image 610 are clearly distinguishable. The photographic image 610 can then be turned into a hard copy to be associated with the container 602. Additionally, the photographic image 610 can be sent to a database 608 to be placed in an electronic file with the order information 612.

In a preferred embodiment, the verification system 600 is fully automated. In this embodiment, the photographic image 610 can be scanned by the computer system to determine the number and spatial orientation of the contents of each container. This information can then be electronically compared to the order form to verify that the order has been filled properly. To aid in the automation of the verification process, containers can be provided with markers, not shown, to indicate to the computer system where in the photographic image it should search to locate the contents of a particular container. Specifically, each container would contain unique identifying indicia, such as a bar code or container number that can be read by the computer system. Each container would also include at least one marker located at one end of the contents of the container to indicate to the computer system exactly where to look in the photograph for the contents of a particular container. Preferably, the marker and the bar code or container number are combined to form a single indicator. Additional markers can be employed, as needed, to further ensure proper verification by, for example, additionally marking the end of the area where the contents of a container can be found.

In another embodiment, the present invention relates to a brachytherapy system. The brachytherapy system includes an order form, one or more packages including a plurality of containers containing the brachytherapy seeds and/or spacers therein, and a photographic image of each of the one or more packages. The order forms, packages, containers and photographic image employed in the system are those as described above. The system has the advantage that the end user can employ the order form and photographic image to verify the order at the end user's location without having to physically handle the radioactive material. In the brachytherapy system, the order form and the photographic image can be provided to the customer separately from the one or more packages, for example, via electronic transmission or other data transmission means, or can be included in the same shipment with the one or more packages.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method for filling and verifying orders for brachytherapy devices, said method comprising the steps of:
   receiving an order;
   loading at least one container with materials according to said order to create at least one loaded container;
   making a photographic image of said at least one loaded container; and
   comparing said photographic image to said order to verify that said order has been properly filled.

2. A method according to claim 1, wherein the method further comprises the steps of:
   dispatching said at least one loaded container to a customer; and
   providing the customer with a copy of said photographic image.

3. A method according to claim 1, wherein said order comprises a form showing a layout of said materials.

4. A method according to claim 1, wherein said photographic image is a digital image.

5. A method according to claim 1, wherein said photographic image is accessible to the customer via the World Wide Web.

6. A method according to claim 1, wherein said materials comprise at least one of a brachytherapy seed, and a biocompatible spacer.

7. A method according to claim 1, wherein said loaded container is selected from the group consisting of a needle, a needle cartridge, a brachytherapy magazine, a radioactive source for the treatment of macular degeneration, an IVBT source, and a strand.

8. A system for verifying an order for a brachytherapy device comprising:
   an order form;
   a photographic imaging device for taking a photographic image of at least one container loaded with brachytherapy devices; and
   apparatus for associating information about said order with said photographic image.

9. A system according to claim 8, further comprising a storage device for storing said photographic image and said information associated with said photographic image.

10. A system according to claim 9, wherein said system further comprises apparatus for allowing viewing of said photographic image and said information associated therewith at a location remote from the location at which said system is located.

11. A system according to claim 9, wherein said loaded container is selected from the group consisting of a needle, a needle cartridge, a brachytherapy magazine, a radioactive source for the treatment of macular degeneration, an IVBT source, and a seed strand.

12. A system according to claim 9, further comprising apparatus for providing a copy of said photographic image to a customer for use in verification of a filled order when said filled order is received by said customer.

13. A system according to claim 9, further comprising apparatus for arranging a plurality of said containers in a predetermined order for including in a single photographic image.

14. A system in accordance with claim 13, wherein said apparatus for associating information about said order with said photographic image provides an order number and a number of the apparatus for arranging a plurality of said containers to said photographic image.

15. A brachytherapy system which comprises:
   at least one container containing at least one radioactive brachytherapy device;
   an order form;
   at least one photographic image of said container which shows the at least one radioactive brachytherapy device; and
   information for associating the order form for a specific order with the at least one photographic image which corresponds to that order.

16. A brachytherapy system as claimed in claim 15, wherein said photographic image is in a digital format.

17. A brachytherapy system as claimed in claim 16, wherein said information comprises an order number.

18. A brachytherapy system as claimed in claim 17, wherein each photographic image shows a plurality of containers arranged in a predetermined order.

19. A brachytherapy system as claimed in claim 18, wherein said system comprises a plurality of sets of containers and a plurality of photographic images including at least one image of each set of containers, and said information comprises information indicating which set of containers a specific photographic image depicts.

* * * * *